(12) United States Patent
Kim et al.

(10) Patent No.: US 10,172,596 B2
(45) Date of Patent: Jan. 8, 2019

(54) BIOLOGICAL TISSUE BIOPSY DEVICE

(71) Applicants: Dongguk University Industry-Academic Cooperation Foundation, Seoul (KR); Catholic University Industry Academic Cooperation Foundation, Seoul (KR)

(72) Inventors: Sung Min Kim, Gyeonggi-do (KR); In Chul Yang, Gyeonggi-do (KR); In Sung Moon, Seoul (KR); Ji Il Kim, Gyeonggi-do (KR); Sun Cheol Park, Seoul (KR); Jeong Kye Hwang, Seoul (KR)

(73) Assignees: Dongguk University Industry-Academic Cooperation Foundation, Seoul (KR); Catholic University Industry Academic Cooperation Foundation, Seoul (KR)

( * ) Notice: Subject to any disclaimer, the term of this patent is extended or adjusted under 35 U.S.C. 154(b) by 325 days.

(21) Appl. No.: 14/769,911

(22) PCT Filed: Jan. 3, 2014

(86) PCT No.: PCT/KR2014/000052
§ 371 (c)(1),
(2) Date: Aug. 24, 2015

(87) PCT Pub. No.: WO2014/129743
PCT Pub. Date: Aug. 28, 2014

(65) Prior Publication Data
US 2016/0007975 A1    Jan. 14, 2016

(30) Foreign Application Priority Data
Feb. 25, 2013 (KR) .................. 10-2013-0020071

(51) Int. Cl.
*A61B 10/02* (2006.01)
*A61M 5/32* (2006.01)
(Continued)

(52) U.S. Cl.
CPC .......... *A61B 10/0275* (2013.01); *A61M 5/32* (2013.01); *A61B 8/0833* (2013.01); *A61B 8/12* (2013.01);
(Continued)

(58) Field of Classification Search
CPC .............. A61B 10/0275; A61B 8/0833; A61B 10/0283; A61B 2017/3413; A61B 2010/0208; A61M 5/32
See application file for complete search history.

(56) References Cited

U.S. PATENT DOCUMENTS 4,134,402 A * 1/1979 Mahurkar ........... A61M 5/1582
604/248
4,850,373 A * 7/1989 Zatloukal ........... A61B 10/0283
600/562
(Continued)

FOREIGN PATENT DOCUMENTS

JP    3198336    6/2001
JP    4460531 B    2/2010
(Continued)

*Primary Examiner* — Angela M Hoffa
(74) *Attorney, Agent, or Firm* — Hammer & Associates, P.C.

(57) ABSTRACT

The present invention relates to a biological tissue biopsy device including a body extending in a longitudinal direction, an outer needle installed to be connected to one side of the body and be extended in a longitudinal direction and including a first tube having a hollow portion formed therein and a second tube disposed in a direction parallel to the first tube to guide a hemostatic substance, an inner needle provided inside the first tube and extending in a longitudinal direction, and a sliding means provided in the body and (Continued)

installed to be connected to one end of the inner needle so as to enable the inner needle to move forward and backward. Here, the sliding means causes the inner needle to move a predetermined distance from the hollow portion of the first tube and be inserted into a target site.

5 Claims, 5 Drawing Sheets

(51) Int. Cl.
    *A61B 8/08*     (2006.01)
    *A61B 8/12*     (2006.01)
    *A61B 10/04*     (2006.01)
    *A61B 17/34*     (2006.01)
    *A61B 17/00*     (2006.01)
    *A61B 90/00*     (2016.01)

(52) U.S. Cl.
    CPC ... *A61B 10/0283* (2013.01); *A61B 2010/0208* (2013.01); *A61B 2010/045* (2013.01); *A61B 2017/0065* (2013.01); *A61B 2017/00495* (2013.01); *A61B 2017/3413* (2013.01); *A61B 2090/3925* (2016.02)

(56) References Cited

U.S. PATENT DOCUMENTS

| | | | | |
|---|---|---|---|---|
| 5,147,335 A * | 9/1992 | Wright | A61B 10/0048 | 600/576 |
| 6,702,760 B2 * | 3/2004 | Krause | A61B 10/0233 | 600/564 |
| 6,849,051 B2 * | 2/2005 | Sramek | A61B 10/025 | 600/565 |
| 8,187,204 B2 * | 5/2012 | Miller | A61B 10/0275 | 600/567 |
| 8,641,641 B2 * | 2/2014 | Cronin | A61B 10/0275 | 600/562 |
| 8,764,680 B2 * | 7/2014 | Rhad | A61B 10/0275 | 600/564 |
| 8,974,400 B2 * | 3/2015 | Swayze | A61B 10/0275 | 600/562 |
| 2003/0055373 A1 * | 3/2003 | Sramek | A61B 10/025 | 604/19 |
| 2008/0306404 A1 * | 12/2008 | Ronald | A61B 10/0275 | 600/564 |
| 2009/0182260 A1 * | 7/2009 | Ronald | A61B 10/0275 | 604/22 |
| 2011/0104280 A1 * | 5/2011 | Hnojewyj | A61B 17/0057 | 424/486 |
| 2011/0245659 A1 * | 10/2011 | Ma | A61B 5/066 | 600/424 |
| 2011/0282241 A1 * | 11/2011 | Swayze | A61B 10/0275 | 600/567 |
| 2011/0282242 A1 * | 11/2011 | Cronin | A61B 10/0275 | 600/567 |
| 2012/0065542 A1 * | 3/2012 | Hibner | A61B 10/0275 | 600/567 |
| 2012/0109007 A1 * | 5/2012 | Rhad | A61B 10/0275 | 600/567 |
| 2013/0225996 A1 * | 8/2013 | Dillard | A61B 10/0283 | 600/439 |
| 2013/0225997 A1 * | 8/2013 | Dillard | A61B 10/0283 | 600/439 |
| 2014/0276209 A1 * | 9/2014 | Hibner | A61B 10/0275 | 600/567 |
| 2015/0305721 A1 * | 10/2015 | Kang | A61B 10/0275 | 600/567 |

FOREIGN PATENT DOCUMENTS

| | | |
|---|---|---|
| KR | 10-1168711 | 7/2012 |
| WO | WO 2010/065736 A2 | 6/2010 |

* cited by examiner

BIOLOGICAL TISSUE BIOPSY DEVICE

BACKGROUND

1. Field of the Invention

The present invention relates to a biological tissue biopsy device used to examine tissues of organs in the human body.

2. Discussion of Related Art

A typical tissue biopsy is an examination performed to check pathologies of the tissue of organs (kidneys, lungs, liver, kidneys, spleen, pancreas, etc.) in the human body.

In this case, the surest way to check the pathologic condition of an organ in the human body is to obtain tissues of the organ and perform a histological examination on the tissues under a microscope.

In recent years, such histological examinations are being actively conducted to check the pathologic condition of the individual organs in the human body. In particular, histological examination is known to be an essential testing method to check the condition of a transplanted organ after organ transplantation.

More specifically, tissues of an organ in the human body are obtained in a clinical trial using a needle specially designed to test the tissues. To obtain the tissues, a percutaneous needle biopsy is typically the conventional test method. By way of example, when tumorous masses are found in the liver or kidneys, the percutaneous needle biopsy is performed to confirm the diagnosis of positive and malignant tumors. Thus, the percutaneous needle biopsy is regularly performed to check the condition of a transplanted kidney or liver after the organ transplantation.

However, the percutaneous needle biopsy performed to confirm a diagnosis has a problem in which bleeding occurs after the histological examination. In a majority of cases, a clotting mechanism in the human body is activated to stop the bleeding naturally. However, when bleeding persists continuously, it may threaten a patient's life.

Therefore, a new tissue biopsy device configured to prevent bleeding complication occurring during the percutaneous needle biopsy often conducted in clinical trials is required.

Researchers have sought to develop a tissue biopsy device that minimizes the risk of bleeding.

SUMMARY OF THE INVENTION

The present invention is directed to providing a biological tissue biopsy device capable of preventing persistent bleeding in an affected part from which a tissue is incised to perform a biopsy or in an organ in the human body in which the bleeding occurs.

Also, the present invention is directed to providing a safe biological tissue biopsy device capable of minimizing or preventing bleeding by stopping the bleeding in an affected part from which a tissue is incised.

One aspect of the present invention provides a biological tissue biopsy device, characterized in that it includes a body extending in a longitudinal direction, an outer needle installed to be connected to one side of the body and extend in a longitudinal direction and including a first tube having a hollow form and a second tube disposed in a direction parallel to the first tube to guide a hemostatic substance, an inner needle provided inside the first tube and extending in a longitudinal direction, and a sliding means provided in the body and installed to be connected to one end of the inner needle so as to enable the inner needle to move forward and backward. Here, the sliding means causes the inner needle to move a predetermined distance from the hollow portion of the first tube and be inserted into a target site.

DETAILED DESCRIPTION OF EXEMPLARY EMBODIMENTS

Figure 1:
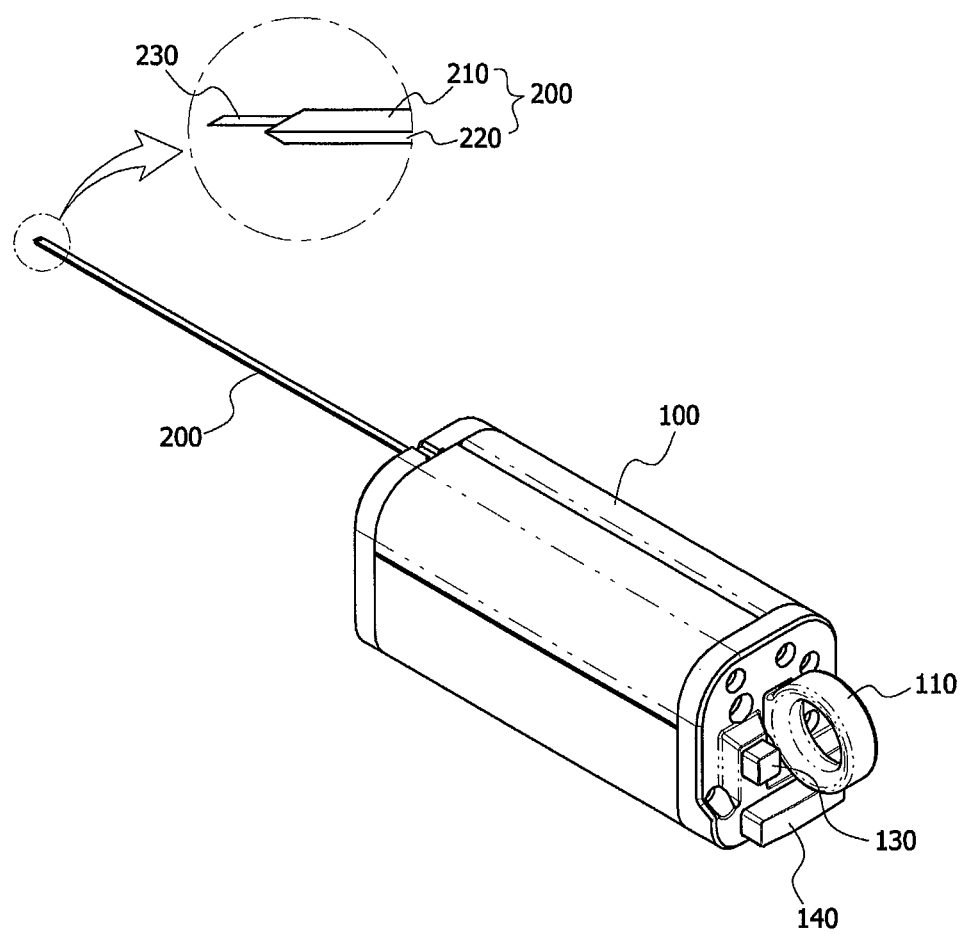
FIG. 1 is a perspective view showing a biological tissue biopsy device according to one exemplary embodiment of the present invention.

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and similarly a second element could be termed a first element, without departing from the scope of the exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to limit exemplary embodiments. The singular forms "a," "an" and "the" are intended to include the plural forms as well, unless the context clearly indicates otherwise. It will be further understood that the terms "comprises," "comprising," "includes" and/or "including" when used herein specify the presence of stated features, integers, steps, operations, elements, components and/or groups thereof, but do not preclude the presence or addition of one or more other features, integers, steps, operations, elements, components and/or groups thereof.

With reference to the appended drawings, the exemplary embodiments of the present invention will be described in detail below. To aid in understanding the present invention, like numbers refer to like elements throughout the description of the figures, and the description of the same elements will be not reiterated.

The present invention provides a biological tissue biopsy device, characterized in that it includes a body extending in a longitudinal direction, an outer needle installed to be connected to one side of the body and extend in a longitudinal direction and including a first tube having a hollow portion formed therein and a second tube disposed in a direction parallel to the first tube to guide a hemostatic substance, an inner needle provided inside the first tube and extending in a longitudinal direction, and a sliding means provided in the body and installed to be connected to one end of the inner needle so as to enable the inner needle to move forward and backward. Here, the sliding means causes the inner needle to move a predetermined distance from the hollow portion of the first tube and be inserted into a target site.

Particularly, the body may include an ultrasonic probe formed at one side thereof, and a safety means formed at the other side thereof to control the sliding means.

In this case, the body may include a hemostatic substance accommodation unit having one side installed to be connected to the second tube and provided inside the body, a piston connected to the other side of the hemostatic substance accommodation unit to be guidably connected to an inner part of the hemostatic substance accommodation unit, and a drive unit provided at the other side of the body and installed to be connected to the piston. Here, the drive unit is manipulated to discharge the hemostatic substance included in the hemostatic substance accommodation unit into the target site via the second tube.

Also, the hemostatic substance accommodation unit may include a first accommodation unit and a second accommodation unit. Here, the first and second accommodation units may include a connection unit configured to connect the second tube and the first and second accommodation units formed at one end of the first and second accommodation units to connect the second tube and the first and second accommodation units.

Meanwhile, the hemostatic substance accommodation unit may be detachable.

According to one exemplary embodiment of the present invention, the inner needle may have at least one groove partially formed on an outer circumferential surface thereof. According to certain exemplary embodiments, one side edge of the border of the groove may include a cut-out portion.

Meanwhile, the inner needle may include a tissue accommodation unit connected to the groove.

Also, the biological tissue biopsy device according to the present invention may further include a vacuum pump provided inside the body and having one side installed to be connected to the inner needle. Here, tissues are sucked into the tissue accommodation unit using suction pressure controlled by the vacuum pump.

Further, the hemostatic substance may be one selected from the group consisting of fibrinogen, a calcium chloride preparation, thrombin, vitamin C, vitamin K, collagen, gelatin, fine gelfoam, and a combination thereof.

Hereinafter, preferred embodiments of the present invention will be described in further detail with reference to the accompanying drawings. Moreover, the sizes or shapes of elements shown in the drawings may be exaggerated for the sake of convenience of description. Also, the terms disclosed below are terms specifically defined in consideration of their configurations and functions in the present invention, and thus may be differently defined according to the users' or operators' intentions or practices. Accordingly, the definitions of the terms should be interpreted based on the contents provided throughout this specification.

Also, it should be understood that the following embodiments presented herein are not intended to limit the scope of the present invention, and other embodiments may be readily practiced within the scope of the present invention by those skilled in the related art to which the present invention belongs, without departing from the scope of the present invention.

Figure 2:
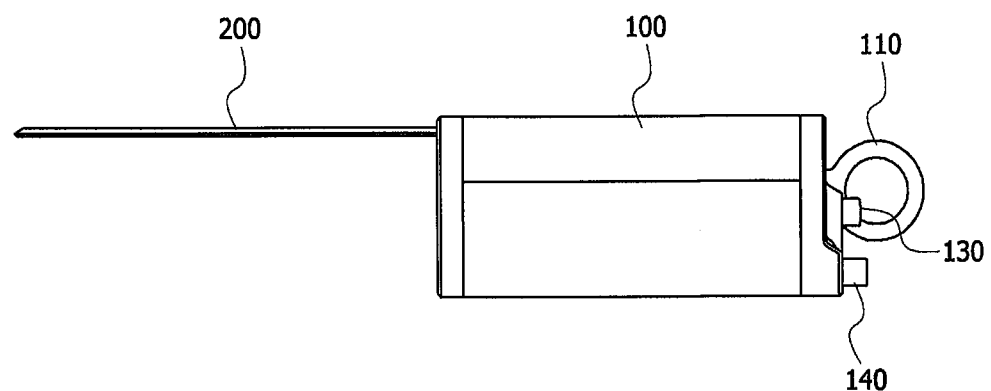
FIG. 2 is a side view showing the biological tissue biopsy device according to one exemplary embodiment of the present invention.
Figure 3:
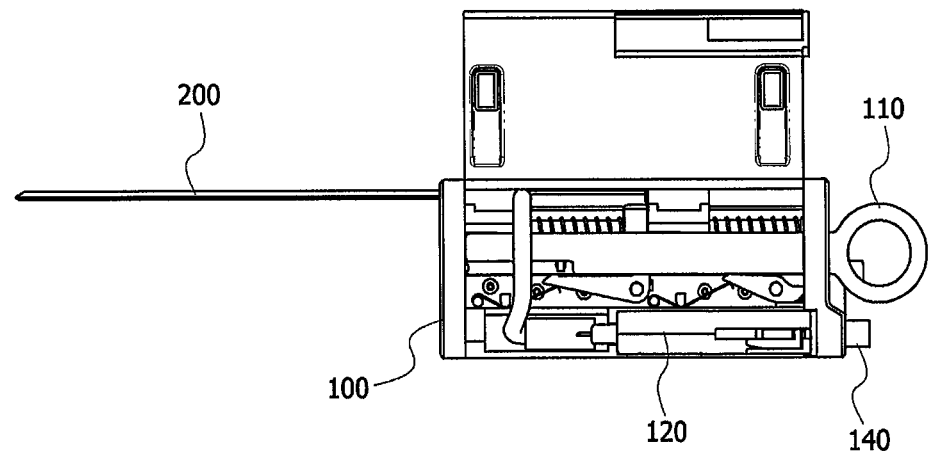
FIG. 3 is a cross-sectional view showing the biological tissue biopsy device according to one exemplary embodiment of the present invention.
Figure 4:
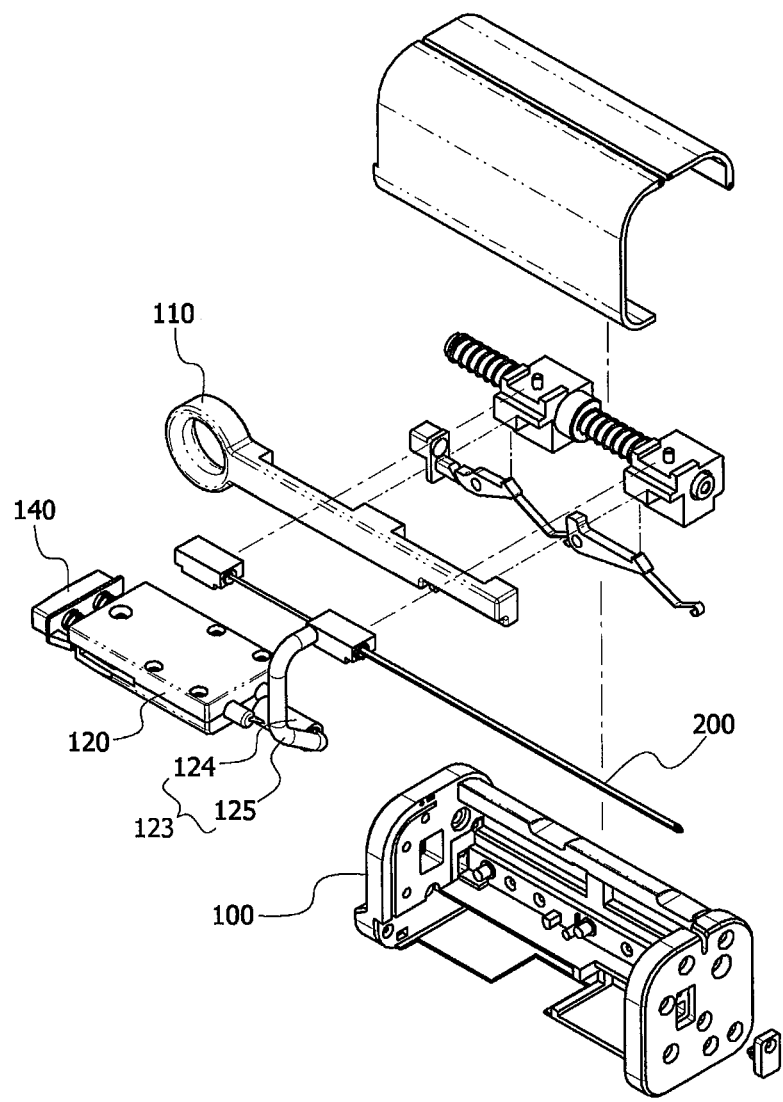
FIG. 4 is an exploded perspective view showing the biological tissue biopsy device according to one exemplary embodiment of the present invention.
Figure 5:
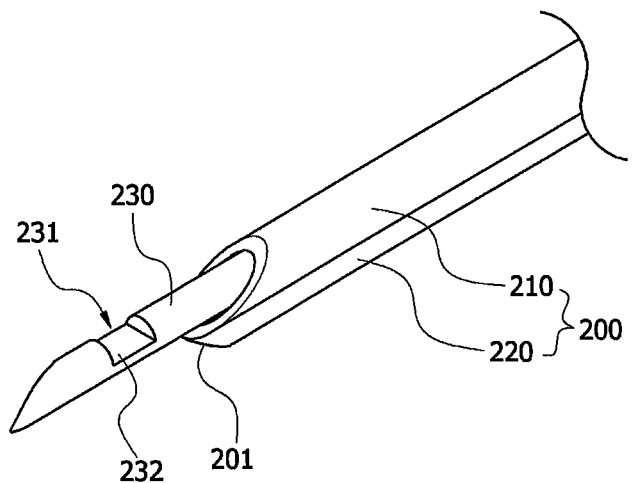
FIG. 5 is an enlarged view showing an outer needle and an inner needle of the biological tissue biopsy device according to one exemplary embodiment of the present invention.
Figure 6:
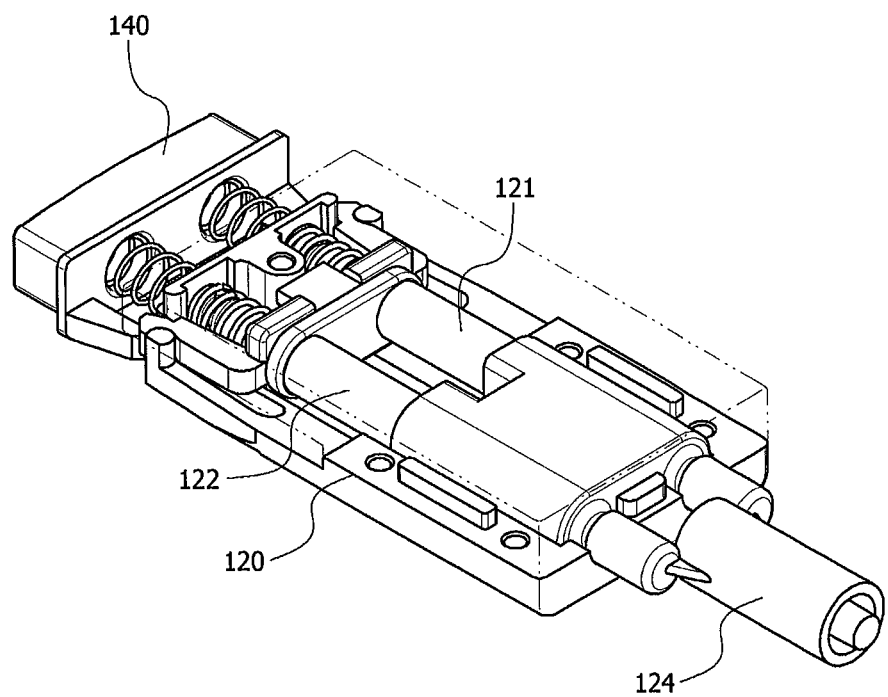
FIG. 6 is an enlarged view showing a hemostatic substance accommodation unit of the biological tissue biopsy device according to one exemplary embodiment of the present invention.
Figure 7:
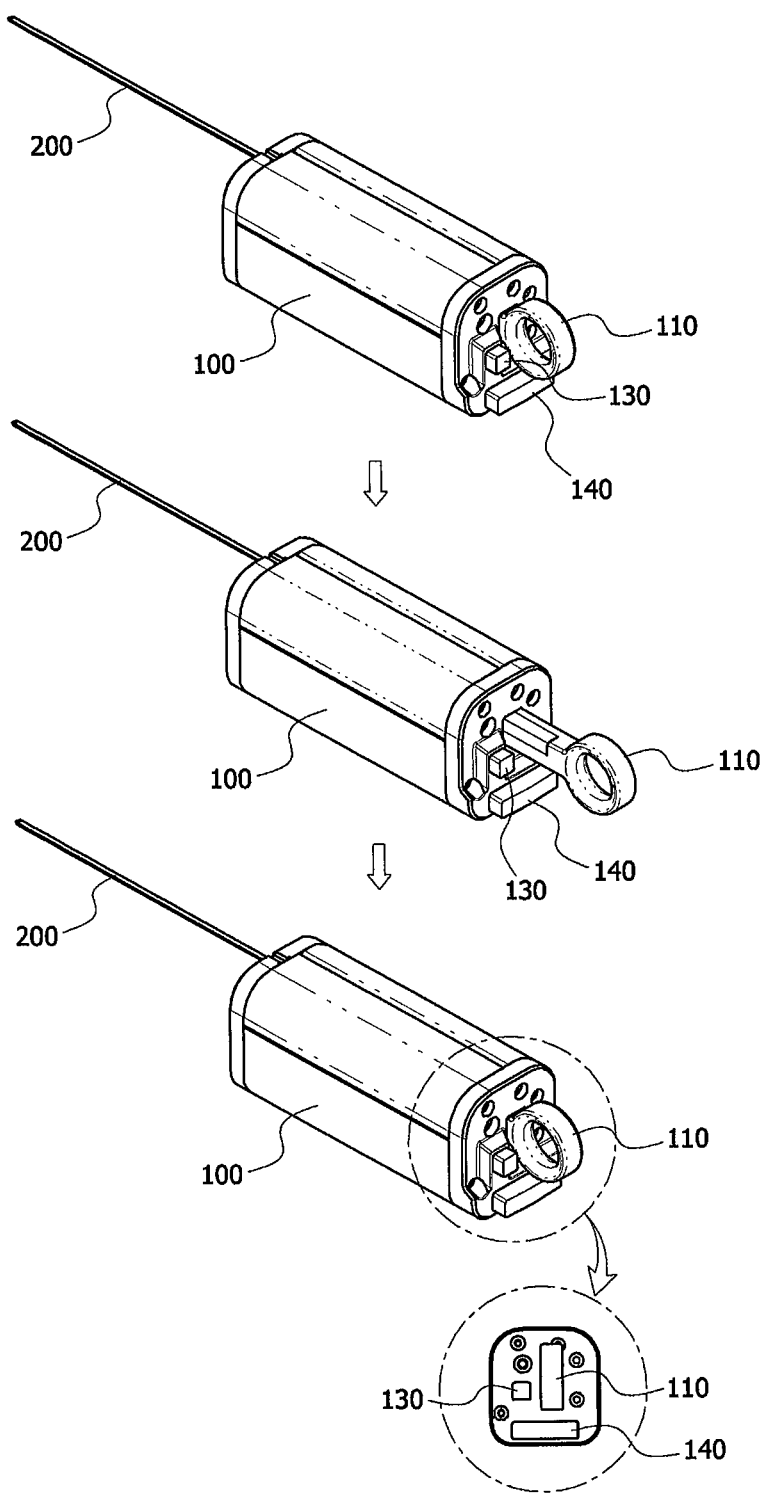
FIG. 7 is a use state diagram showing the biological tissue biopsy device according to one exemplary embodiment of the present invention.

FIG. 1 is a perspective view showing a biological tissue biopsy device according to one exemplary embodiment of the present invention, FIG. 2 is a side view showing the biological tissue biopsy device according to one exemplary embodiment of the present invention, FIG. 3 is a cross-sectional view showing the biological tissue biopsy device according to one exemplary embodiment of the present invention, FIG. 4 is an exploded perspective view showing the biological tissue biopsy device according to one exemplary embodiment of the present invention, FIG. 5 is an enlarged view showing an outer needle and an inner needle of the biological tissue biopsy device according to one exemplary embodiment of the present invention, FIG. 6 is an enlarged view showing a hemostatic substance accommodation unit of the biological tissue biopsy device according to one exemplary embodiment of the present invention, and FIG. 7 is a use state diagram showing the biological tissue biopsy device according to one exemplary embodiment of the present invention. Hereinafter, the biological tissue biopsy device according to one exemplary embodiment of the present invention will be described in detail with reference to FIGS. 1 to 7 and the embodiments.

As described above, the present invention relates to a biological tissue biopsy device capable of preventing the occurrence of persistent bleeding when a tissue of an affected part for use in biopsies is incised.

As shown in FIGS. 1 to 7, the biological tissue biopsy device includes a body 100, an outer needle 200, an inner needle 230, and a sliding means 110.

More particularly, the body 100 has an outer needle 200 formed at one side thereof to extend in a longitudinal direction. According to certain exemplary embodiments, the outer needle 200 is composed of two tubes having a hollow portion formed in a longitudinal direction thereof. Among the two tubes, one tube is referred to as a first tube 210, and the other tube is referred to as a second tube 220.

The first tube 210 and the second tube 220 are disposed parallel to each other. In this case, the inner needle 230 extending in a longitudinal direction may be included inside the first tube 210, and the second tube 220 may serve to guide a hemostatic substance. Particularly, an internal diameter of the second tube 220 may be smaller than an internal diameter of the first tube 210, a configuration which is provided for the purpose of minimizing the damage of tissues.

Also, a sliding means 110 installed to be connected to the one end of the inner needle 230 to enable the inner needle 230 to move forward and backward may be included on one side of the body 100. Therefore, the inner needle 230 may move a predetermined distance from the hollow portion of the first tube 210 and be inserted into a target site by means of the sliding means 110.

Particularly, the body 100 may include an ultrasonic probe formed at one side thereof, and may extend in a longitudinal direction. The ultrasonic probe serves to accurately locate the target site from which tissues are to be obtained.

Also, a safety means 130 configured to control the sliding means 110 may be included on the other side of the body 100.

Here, the body 100 may refer to a handle typically used in the related art, and is easily formed to extend in a longitudinal direction so that the body 100 may be grasped by a hand.

Also, the target site may be an affected part to be biopsied, or an organ, tissue or neoplasm in the human body.

The body 100 according to the present invention includes a hemostatic substance accommodation unit 120, and a drive unit 140. In this case, the hemostatic substance accommodation unit 120 is provided inside the body 100. Here, one side of the hemostatic substance accommodation unit 120 may be installed to be connected to the second tube 220, and the other side may be installed to be connected to a piston configured to apply pressure to an inner part of the hemostatic substance accommodation unit 120. In this case, the piston may be guidably connected to the inner part of the hemostatic substance accommodation unit. More particularly, the hemostatic substance accommodation unit 120 may be in the form of a syringe in which a hemostatic substance is accommodated, and may include a connection unit 123 at a position at which the hemostatic substance accommodation unit 120 is connected to the second tube 220.

Also, the drive unit 140 may be included on the other side of the body 100, and the drive unit 140 may be installed to be connected to the piston. Particularly, since the piston is installed to be connected to the drive unit 140, the piston may be activated to discharge a hemostatic substance into the second tube 220 and introduce the hemostatic substance into a target site when the drive unit 140 is driven by a transplantation operator.

In this case, the hemostatic substance accommodation unit 120 is characterized in that it may be detached so that a hemostatic substance can be loaded and used. A hemostatic substance display unit on which the quantity of the hemostatic substance may be provided on a portion of the hemostatic substance accommodation unit 120.

Here, the hemostatic substance refers to a hemostatic substance widely used in clinical trials, and may include thrombin, gelform, or fibrin glue. In addition, the hemostatic substance may include a calcium chloride preparation, thrombin, vitamin C, vitamin K, collagen, gelatin, or fine gelfoam.

Particularly, according to one exemplary embodiment of the present invention, the hemostatic substance accommodation unit 120 may include two syringes, as shown in FIG. 6. In the present invention, one syringe refers to a first accommodation unit 121, and the other syringe refers to a second accommodation unit 122. More particularly, one end of the first accommodation unit 121 and the second accommodation unit 122 may include a connection unit 123 configured to connect the second tube 220 to the first and second accommodation units 121 and 122. Also, the connection unit 123 may include a connection tube 125, and a spray nozzle 124. In this case, the first accommodation unit 121 and the second accommodation unit 122 may accommodate two different types of hemostatic substances. When the drive unit 140 is manipulated to discharge the hemostatic substances, which have been accommodated in the first and second accommodation units, into the connection unit 123 at the same time, the two types of the hemostatic substances may be mixed at the same ratio, and discharged into the second tube 220. By way of example, a fibrinogen concentrate may be accommodated in the first accommodation unit 121, and thrombin may be accommodated in the second accommodation unit 122.

Also, the outer needle 200 according to the present invention is characterized in that the outer needle 200 has a tip portion 201 formed at the front end thereof. Here, the tip portion 201 refers to a front end or a bit, and may be formed in a pointed shape to promote insertion of the outer needle 200 into the target site.

In addition, the inner needle 230 according to the present invention is provided in the hollow portion of the first tube 210 of the outer needle 200 to extend in a longitudinal direction, and at least one groove 231 may be formed on an outer circumferential surface of the inner needle 230. Also, a tissue accommodation unit connected to the groove 231 may be included at an inner part of the inner needle 230. In addition, a cut-out portion 232 formed in the form of a blade to readily incise a tissue may be included at one side edge of the border of the groove 231.

Further, the biological tissue biopsy device according to the present invention is characterized in that it includes a vacuum pump having one side installed to be connected to the inner needle 230 and provided inside the body 100. Here, tissues are sucked by suction pressure controlled by the vacuum pump.

The operation and effects of the biological tissue biopsy device having a configuration according to one exemplary embodiment of the present invention will be described as follows.

First, the outer needle 200 is inserted into a target site to be biopsied, and an end of the outer needle 200 is positioned close to the target site. In this case, the position of the target site may be checked using the ultrasonic probe. Here, the target site also refers to an affected part.

Next, the sliding means 110 is driven to force the inner needle 230 to enter an affected part, and incise some of a target site to be biopsied, that is, a tissue. In this case, the safety means 130 disposed at the other side of the body 100 may be driven to control the sliding means 110.

Also, tissues may be incised by the cut-out portion 232 formed in the groove 231 on the outer circumferential surface of the inner needle 230, and may be accommodated in the tissue accommodation unit connected to the groove 231. Meanwhile, the tissues may be sucked into the tissue accommodation unit using suction pressure controlled by the vacuum pump provided inside the body 100 after the tissue is incised.

At the same time, the drive unit 140 is driven to discharge the hemostatic substance in the hemostatic substance accommodation unit 120 into the second tube 220 and introduce the hemostatic substance into the affected part, thereby stopping the bleeding at the site of the bleeding.

As described above, when the incision of the tissue and the arrest of bleeding are completed, the outer needle 200 is removed and a surgical procedure is completed.

In this way, bleeding occurs in the affected part from which the tissue is incised. When the persistent bleeding occurs, the hemostatic substance may be introduced to stop the bleeding quickly.

The biological tissue biopsy device according to one exemplary embodiment of the present invention can be useful in effectively stopping bleeding in a tissue-incised site, or a site of bleeding of an organ in the human body.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A biological tissue biopsy device comprising:
   a body extending in a longitudinal direction;
   an outer needle connected to one side of the body and extending in a longitudinal direction and comprising a first tube having a hollow portion formed therein and a second tube having a smaller diameter than the first tube, disposed adjacent to the first tube and disposed in a direction parallel to the first tube to guide a hemostatic substance;
   an inner needle provided inside the first tube and extending in the longitudinal direction of the outer needle and including at least one groove partially formed on an outer circumferential surface thereof;
   a handle provided in the body and connected to one end of the inner needle so as to enable the inner needle to move around,
   a hemostatic substance syringe having one side connected to the second tube and provided inside the body;
   a piston connected to the other side of the hemostatic substance syringe and guidably connected to an inner part of the hemostatic substance syringe; and
   a button provided on the body and connected to the piston,
   wherein the hemostatic substance syringe comprises a first syringe, a second syringe, and a connection tube that connects the second tube to the first and second syringes,
   wherein the first and second syringes each accommodate different types of hemostatic substances,
   wherein the handle is adapted to cause the inner needle to move a predetermined distance from the hollow portion of the first tube and be inserted into a target site,
   wherein the button is adapted to discharge the hemostatic substances included in the hemostatic substance syringe into the target site via the second tube,
   wherein the outer needle has a tip portion defined by the first tube and second tube at a distal end of the outer needle and the tip portion tapers to the center of the outer needle.

2. The biological tissue biopsy device according to claim 1, wherein the hemostatic substance syringe is detachable from the body.

3. The biological tissue biopsy device according to claim 1, wherein one side edge of the border of the groove comprises a cut-out portion.

4. The biological tissue biopsy device according to claim 1, further comprising a vacuum pump provided inside the body and having one side connected to the inner needle.

5. The biological tissue biopsy device according to claim 1, wherein the hemostatic substances are is one selected from the group consisting of fibrinogen, a calcium chloride preparation, thrombin, vitamin C, vitamin K, collagen, gelatin, and a combination thereof.

* * * * *